US009216932B2

(12) United States Patent
Zhai et al.

(10) Patent No.: US 9,216,932 B2
(45) Date of Patent: *Dec. 22, 2015

(54) DEHALOGENATION OF TRANS-1-CHLORO-3,3,3-TRIFLUOROPROPENE

(71) Applicant: Honeywell International, Inc., Morristown, NJ (US)

(72) Inventors: Yian Zhai, Williamsville, NY (US); Andrew J. Poss, Kenmore, NY (US); Rajiv R. Singh, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,303

(22) Filed: May 5, 2014

(65) Prior Publication Data
US 2014/0343330 A1 Nov. 20, 2014

Related U.S. Application Data

(60) Provisional application No. 61/825,402, filed on May 20, 2013.

(51) Int. Cl.
C07C 17/00 (2006.01)
C07C 17/25 (2006.01)
(52) U.S. Cl.
CPC .............. C07C 17/25 (2013.01); *C07B 2200/09* (2013.01)
(58) Field of Classification Search
CPC .......... C07C 17/25; C07C 21/22; C07C 17/23
USPC .................................................. 570/156, 155
See application file for complete search history.

(56) References Cited

U.S. PATENT DOCUMENTS

| 5,616,819 | A | 4/1997 | Boyce et al. |
| 6,844,475 | B1 | 1/2005 | Tung et al. |
| 6,958,424 | B1 | 10/2005 | Nair et al. |
| 2008/0103342 | A1 | 5/2008 | Wang et al. |
| 2010/0145112 | A1 | 6/2010 | Ishihara et al. |
| 2011/0288346 | A1* | 11/2011 | Poss et al. ..................... 570/154 |

FOREIGN PATENT DOCUMENTS

WO  WO 20101059496 A1  5/2010
WO  WO 2010/095764 al  *  8/2010

OTHER PUBLICATIONS

Eur. J. Org. Chem. 2009, 4395-4399.
Organomet. 2003, 5534.
J. Flu. Chem. 36(3), 313-17; 1987.
J. Org. Chem. 1963, 28, 1139-40.

* cited by examiner

*Primary Examiner* — Jafar Parsa
(74) *Attorney, Agent, or Firm* — Bruce O. Bradford

(57) ABSTRACT

The present invention is related to making hydrofluorocarbons (HCFCs), more specifically, 3,3,3-trifluoropropyne (TFP), from trans-1-chloro-3,3,3-trifluoropropene (trans-1233zd) by contacting the trans-1233zd with a base. Preferably, the base is potassium hydroxide or potassium tert-butoxide, which may or may not be dissolved in as solvent.

14 Claims, No Drawings

DEHALOGENATION OF TRANS-1-CHLORO-3,3,3-TRIFLUOROPROPENE

CROSS-REFERENCE TO RELATED APPLICATIONS

This application claims domestic priority from commonly owned U.S. Provisional Application Ser. No. 61/825,402 filed 20 May 2013, the disclosure of which is hereby incorporated herein by reference.

FIELD OF THE INVENTION

The present invention is related to making hydrofluorocarbons (HCFCs), more specifically, 3,3,3-trifluoropropyne (TFP), from trans-1-chloro-3,3,3-trifluoro-propene (trans-1233zd).

BACKGROUND OF THE INVENTION

Chlorofluorocarbons (CFCs) are known and widely used in the industry as solvents, blowing agents, heat transfer fluid, aerosol propellants, and for other uses. However, CFCs are also well-known to have ozone depletion potential (ODP) and are regulated by the Montreal Protocol. A suitable replacement material would have negligible or no ODP, as well as an acceptable global warming potential (GWP).

For example, 1-chloro-3,3,3-trifluoropropene (1233zd) is a chlorofluoroolefin with zero GWP and negligible ODP, which makes it very useful in foaming, aerosol and refrigeration applications. Cis-1233zd is much more preferred than its trans isomer ("trans-1233zd") in solvent applications due to its higher boiling point. While various methods can be used to make 1233zd (see, e.g., U.S. Pat. No. 6,958,424, U.S. Pat. No. 6,844,475, U.S. Pat. No. 5,616,819, US 2008/0103342, WO 2010/059496), trans-1233zd is the thermal dynamically favored product in such conventional manufacturing processes, with only 3-5% of cis isomer being typically formed.

Some higher efficiencies have been achieved in the laboratory with the use of 3,3,3-trifluoropropyne (TFP) as a feedstock. The major problem with such protocols is that such TFP feedstocks are not available in large quantities. Accordingly, efforts have been made to improve TFP production processes, including efforts related to the use of the less desired trans-1233zd isomer.

For example, in one process trans-1233zd is treated with LDA (lithium diisopropylamide) or MeLi (methyl lithium) at −80° C. to obtain trifluoroacetylenic lithium salt (*Eur. J. Org. Chem.* 2009, 4395-4399), which can be hydrolyzed to TFP. This TFP lithium salt can also be obtained by deprotonating $CF_3CH_2CHF_2$ (245fa) with n-butyl lithium (*Organomet.* 2003, 5534) in ether.

As an additional example, U.S. Pat. No. 8,791,309, describes a process using sodium amide as base for dehydrochlorination of trans-1233zd in ether or ammonia to produce 3,3,3-trifluoropropyne. However, such processes are expensive to implement on a commercial scale owing to operating conditions and/or the toxicity and/or hazardous nature of reactants.

Commercial processes for producing TFP not using trans-1233zd also have disadvantages. For example, 1,1,2-trichloro-3,3,3-trifluoropropene treated with zinc in DMF at 100° C. followed by hydrolysis with water can provide a 75% yield of TFP (*J. Flu. Chem.* 36(3), 313-17; 1987; *J. Org. Chem.* 1963, 28, 1139-40); however, the synthesis of 1,1,2-trichloro-3,3,3-trifluoro-propene requires a multiple step reaction, and is not commercially available in large quantities. Furthermore, the use of zinc in the process can lead to environmentally related expenses.

Accordingly, there remains a need to safely and economically produce TFP on a commercial scale.

SUMMARY OF THE INVENTION

The present inventors have found that by contacting trans-1233zd with a potassium containing base, e.g., potassium hydroxide (KOH) or potassium tert-butoxide (KO*t*Bu), TFP can be economically and safely produced at relatively high yield.

In accordance with a first aspect of the present invention, a method for producing 3,3,3-trifluoropropyne from trans-1233zd by contacting with potassium hydroxide is provided.

In accordance with a second aspect of the present invention, a method for producing 3,3,3-trifluoropropyne from trans-1233zd by contacting with potassium tert-butoxide is provided.

It should be appreciated by those persons having ordinary skill in the art to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

In accordance with a first preferred embodiment of the present invention, trans-1233zd is reacted with a basic composition comprising potassium hydroxide to produce TFP. One advantage of such a process is that all of the starting materials in accordance with this embodiment are generally commercially available. For example, potassium hydroxide is commercially available and widely used in chemical industries. Ether, ethanol (or EtOH), butanol (or n-BuOH) and tert-butanol (or t-BuOH), and tetrahydrofuran (or THF), are commercially available solvents, and have the additional benefit of being recyclable.

It is preferable that the molar ratio of potassium hydroxide to trans-1233zd should be at least two, and can be higher, but ratios in excess of 10 are not particularly advantageous, and might make side-reactions more common. Molar ratios in the range of 3 to 5 are particularly preferred. Other bases may additionally be used, for example, calcium oxide; in this case, it is preferred that the molar ratio of base (e.g., (KOH+CaO)) to trans-1233zd be maintained in the same ratios as above.

In a preferred reaction, potassium hydroxide is dissolved in tert-butanol in a three necked flask and heated to reflux. Then 1233zd in ether is added slowly through an addition funnel. After addition was complete, the mixture is stirred for another one to two hour at reflux to drive the product out. The product is then collected in a −70° C. dry-ice acetone trap through a reflux condenser. Finally, NMR, GCMS and GC are used to identify the products.

In a second preferred embodiment, a stronger base, i.e., potassium tert-butoxide is used instead of potassium hydroxide, and procedures similar to the above are used.

The following examples provide additional details regarding various embodiments of the present invention.

Example 1

35.1 g of KOH pellets (88%, 0.552 mol) and 5.0 g of CaO (89.3 mmol) powder were grinded under nitrogen, and this fine powder mixture was added into a three-necked flask equipped with a mechanical stirrer and reflux condenser which was controlled at −11° C. The KOH mixture was heated in oil bath to 110-120° C., and 39.0 g of trans-1233zd in 20 mL diethyl ether was added slowly with stirring through an addition funnel. Products out of the reaction flask were collected in −70° C. trap and analyzed with GC. Sample (8.7 g) in the cold trap contained 52.1% of 3,3,3-trifluoropropyne, 39.29% of trans-1233zd, 8.44% diethyl ether and other unidentified compounds. The liquid sample (37.5 g) remaining in the reaction flask contained 0.84% 3,3,3-trifluoropropyne, 47.85% of trans-1233zd, 50.11% diethyl ether and some other impurities. The calculated TFP yield was 16.3% according to trans-1233zd.

Different KOH/CaO ratios were tried with or without solvents; results are listed in Table 1 below.

TABLE 1

| Entry | Base KOH/CaO Mole ratio | Solvent | Temperature (° C.) | Result (% TFP yield) |
|---|---|---|---|---|
| 1 | 6.2/1 | None, ether as distillate | 110 | 16.3%, most starting material and some propyne (0.8%) remain in flask |
| 2 | 9/1 | None | 110 | Difficult to operate |
| 3 | 9/1 | Diglyme | 110 | Product is destroyed |
| 4 | 6.2/1 | None, ether as distillate | 110 | 13.6%, material left in flask contains 1.2% propyne |
| 5 | 4.5/1 | DME | 110 | Propyne is destroyed and difficult to operate |

Example 2

Potassium hydroxide (powder, 31.6 g, 88%, 0.496 mol) and Aliquat 336 (1.0 g) were dissolved in 42.0 g of tert-butanol in a three necked flask and heated to reflux, 1233zd (19.0 g, 0.146 mol) in ether (17 ml) was added dropwise through an addition funnel. After addition was complete, the mixture was stirred for another one to two hour at reflux to drive the product out. The product (9.2 g clear liquid) was collected in the −70° C. dry-ice acetone trap through a reflux condenser cooled by water. GC showed 40.25% of 3,3,3-trifluoropropyne, 42.61% trans-1233zd, and 15.82% ether along with some minor impurities. The calculated yield was 28.9% according to trans-1233zd.

The mother liquor in the reaction flask was checked by GC, which contained tert-butanol, trans-1233zd, ether and some 3,3,3-trifluoropropyne.

Other solvents such as ethanol, n-butanol, tetrahydrofuran (THF), ethanol (EtOH), as well as a stronger base—i.e., potassium tert-butoxide—were tried in this reaction; the results are listed in Table 2 below:

TABLE 2

| Entry | Base | Solvent | Bath Temperature (° C.) | Result (% TFP yield) |
|---|---|---|---|---|
| 1 | KOH | t-BuOH | 110 | 27.5% |
| 2 | KOH | t-BuOH | 110 | 29.0% |
| 3 | KOH | n-BuOH | 110 | Destroyed SM |
| 4 | KO$^t$Bu | t-BuOH | 68 | 7%, SM most destroyed; adding THF does not help |
| 5 | KO$^t$Bu | THF | 68 | 28.5% |
| 6 | KOH | EtOH | 110 | 2.2% |
| 7 | KO$^t$Bu/ Aliquat | t-BuOH | 110 | 28.9%, more product is destroyed from the mixture color |

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A method of making 3,3,3-trifluoropropyne from trans-1-chloro-3,3,3-trifluoropropene, the method comprising the steps of:
   providing a first composition comprising potassium hydroxide;
   contacting said first composition with a second composition comprising trans-1-chloro-3,3,3-trifluoropropene to make a third composition comprising 3,3,3-trifluoropropyne; and
   wherein the first composition is heated to reflux temperature prior to contacting the first composition with the second composition.

2. The method of claim 1, wherein the first composition further comprises calcium oxide.

3. The method of claim 1, wherein the first composition further comprises tert-butanol.

4. The method of claim 1, further comprising the step of obtaining a fourth composition comprising 3,3,3-trifluoropropyne from the third composition by maintaining the third composition at reflux temperature and collecting a fourth composition which has a higher concentration of 3,3,3-trifluoropropyne than said third composition.

5. The method of claim 1, wherein the molar ratio of potassium hydroxide contacted with trans-1-chloro-3,3,3-trifluoropropene is at least 2.

6. The method of claim 1, wherein the molar ratio of potassium hydroxide contacted with trans-1-chloro-3,3,3-trifluoropropene is between 3 and 5.

7. A method of making 3,3,3-trifluoropropyne from trans-1-chloro-3,3,3-trifluoropropene, the method comprising the steps of:
provides a first composition comprising potassium hydroxide;
contacting said first composition with a second composition comprising trans-1-chloro-3,3,3-trifluoropropene to make a third composition comprising 3,3,3-trifluoropropyne;
wherein the first composition optionally further comprises calcium oxide;
wherein the first composition optionally further comprises tert-butanol; and wherein the first composition is heated to reflux temperature prior to contacting the first composition with the second composition.

8. A method of making 3,3,3-trifluoropropyne from trans-1-chloro-3,3,3-trifluoropropene, the method comprising the steps of:
providing a first composition comprising potassium tert-butoxide dissolved in a solvent;
contacting said first composition with a second composition comprising trans-1-chloro-3,3,3-trifluoropropene to make a third composition comprising 3,3,3-trifluoropropyne; and
wherein the first composition is heated to reflux temperature prior to contacting the first composition with the second composition.

9. The method of claim 8, wherein the first composition comprises tetrahydrofuran.

10. The method of claim 8, wherein the first composition comprises tert-butanol.

11. The method of claim 8, further comprising the step of obtaining a fourth composition comprising 3,3,3-trifluoropropyne from the third composition by maintaining the third composition at reflux temperature and collecting a fourth composition which has a higher concentration of 3,3,3-trifluoropropyne than said third composition.

12. The method of claim 8, wherein the molar ratio of potassium tert-butoxide contacted with trans-1-chloro-3,3,3-trifluoropropene is at least 2.

13. The method of claim 8, wherein the molar ratio of potassium tert-butoxide contacted with trans-1-chloro-3,3,3-trifluoropropene is between 3 and 5.

14. A method of making 3,3,3-trifluoropropyne from trans-1-chloro-3,3,3-trifluoropropene, the method comprising the steps of:
providing a first composition comprising potassium tert-butoxide dissolved in a solvent;
contacting said first composition with a second composition comprising trans-1-chloro-3,3,3-trifluoropropene to make a third composition comprising 3,3,3-trifluoropropyne;
wherein the first composition optionally comprises tetrahydrofuran; wherein the first composition optionally comprises tert-butanol; and
wherein the first composition is heated to reflux temperature prior to contacting the first composition with the second composition.

* * * * *